US008377309B2

(12) United States Patent
Steinecker

(10) Patent No.: US 8,377,309 B2
(45) Date of Patent: Feb. 19, 2013

(54) METHODS AND APPARATUS FOR MAKING A CHROMATOGRAPHY COLUMN

(75) Inventor: William H. Steinecker, Farmersville, OH (US)

(73) Assignee: Nobull Innovation LLC, Dayton, OH (US)

( * ) Notice: Subject to any disclaimer, the term of this patent is extended or adjusted under 35 U.S.C. 154(b) by 238 days.

(21) Appl. No.: 12/947,528

(22) Filed: Nov. 16, 2010

(65) Prior Publication Data

US 2012/0118156 A1    May 17, 2012

(51) Int. Cl.
*B01D 15/08* (2006.01)
(52) U.S. Cl. ............... 210/656; 210/198.2; 96/101
(58) Field of Classification Search .......... 210/635, 210/656, 659, 198.2; 95/82, 88; 96/101
See application file for complete search history.

(56) References Cited

U.S. PATENT DOCUMENTS

| | | | |
|---|---|---|---|
| 5,135,549 | A | 8/1992 | Phillips et al. |
| 6,783,680 | B2 | 8/2004 | Malik |
| 6,838,640 | B2 | 1/2005 | Wise et al. |
| 8,117,895 | B2 | 2/2012 | Currie et al. |
| 2009/0139934 | A1 | 6/2009 | Steinecker et al. |
| 2009/0308137 | A1 | 12/2009 | Currie et al. |
| 2012/0048108 | A1 | 3/2012 | Steinecker |
| 2012/0118805 | A1 | 5/2012 | Steinecker |
| 2012/0118806 | A1 | 5/2012 | Steinecker |

FOREIGN PATENT DOCUMENTS

| | | |
|---|---|---|
| WO | 02/072225 | 9/2002 |
| WO | 2009/073270 | 6/2009 |

OTHER PUBLICATIONS

Nakai, T. et al., "Micro-fabricated semi-packed column for gas chromatography by using functionalized parylene as a stationary phase," *J. Micromech. Microeng.*, 19, 065032 (6 pp) (2009).
Lambertus, G. et al., "Design, Fabrication, and Evaluation of Microfabricated Columns for Gas Chromatography," *Anal. Chem.*, 76, pp. 2629-2637 (2004).
Reidy, S. et al., "High-Performance, Static-Coated Silicon Microfabricated Columns for Gas Chromatography," *Anal. Chem.*, 78, pp. 2623-2630 (2006).
US, Notice of Allowance, U.S. Appl. No. 12/947,374 (Aug. 6, 2012).
US, Notice of Allowance, U.S. Appl. No. 12/947,435 (Aug. 8, 2012).

*Primary Examiner* — Ernest G Therkorn
(74) *Attorney, Agent, or Firm* — Thompson Hine LLP

(57) ABSTRACT

Methods for depositing a stationary phase in a tube for chromatography, in particular, as a variable gradient column are disclosed. The methods include providing a tube having a first end and a second end, the tube containing a fluid composition comprising a stationary phase precursor and a solvent, connecting the first end of the tube to a flow device, removing the solvent from a meniscus of the fluid composition, the solvent exiting the tube at the second end, and operating the flow device while removing the solvent such that the amount of the stationary phase precursor deposited within the tube changes as the meniscus retreats within the tube to deposit a stationary phase having a thickness gradient along the length of the interior of the tube.

13 Claims, 11 Drawing Sheets

METHODS AND APPARATUS FOR MAKING A CHROMATOGRAPHY COLUMN

TECHNICAL FIELD

The present invention relates generally to methods and apparatus for making a chromatography column for differential acceleration separations. More particularly, the invention relates generally to methods and apparatus for depositing a stationary phase film or coating on the inner walls of an open tube of any cross-sectional profile with a gradually reducing film thickness from one end of the tube to another, or depositing a constant thickness of the stationary phase within a tube that has a gradually enlarging cross-sectional area.

BACKGROUND

Open tubular columns (OTCs) have been in use in chromatography for several decades. They typically consist of an inert tube with a stationary phase deposited on the inner walls with a constant cross-sectional area along the length of the tube. The stationary phase provides a partitioning phase that permits chemical separation of bands of analyte molecules carried in the mobile phase passed therethrough. The dimensions of the tube, thickness of the stationary phase, and composition of the stationary phase are chosen by the chromatographer to produce the desired separation.

To form OTCs, two methods are generally used to deposit stationary phase inside the open tube; dynamic and static stationary phase deposition. In a dynamic coating process, a plug of solvent, containing dissolved materials that will become the stationary phase, is flowed through the tube such that the dissolved material is left on the inner wall of the tube forming the initial form of the stationary phase film or coating. In some cases, additional treatment steps are implemented, such as heating and drying. These steps seek to condition or chemically alter the residual stationary phase film or active sites in the tube until the desired characteristics are provided to the stationary phase. Dynamic coating is often not preferred because it is difficult to control and therefore less economic for column production.

In contrast, static coating allows direct, relatively accurate, estimation of the deposited film thickness and can also produce a more uniform film. In static coating methods, one or more materials that will become the stationary phase are suspended or dissolved in a liquid that is used to fill the tube that will become the OTC. One end of this tube is sealed off and the other connected to a vacuum source. In some approaches, a temperature bath may be used to maintain the temperature of the filled tube. The liquid is then allowed to evaporate, which may be include the use of a low-pressure vacuum source. During evaporation, the meniscus (air/liquid interface inside the tube) retreats and leaves behind a residual film of the material(s) that will become the stationary phase. The residual film may then be further chemically treated, conditioned, etc to form the final stationary phase.

Variable Geometry Columns (VGC) are disclosed in U.S. Patent Publication No. 2009/0139934 to Steinecker et al., herein incorporated by reference in its entirety. That patent application discusses chromatography columns that produce differential acceleration based separations by several mechanisms. Some proposed mechanisms include increasing the cross-section of the column toward the column outlet, changing the thickness or other composition of stationary phase within the column, and providing a temperature and/or mobile phase velocity gradient along the column. Methods and apparatus for efficiently and cost-effectively making VGCs are disclosed herein.

SUMMARY

In one aspect, the invention includes various methods of depositing a stationary phase thickness, such as a film or coating, in a tube, in particular, to form a variable geometry column for differential acceleration chromatographic separation of analytes including faster separation times. The methods include providing a tube having a first end and a second end, the tube containing a fluid composition comprising a stationary phase precursor and a solvent, connecting the first end of the tube to a flow device, removing the solvent from a meniscus of the fluid composition, the solvent exiting the tube at the second end, and operating the flow device while removing the solvent such that the amount of the stationary phase precursor deposited within the tube changes as the meniscus retreats within the tube to deposit a stationary phase having a thickness gradient along the length of the interior of the tube.

In one embodiment, the tube has a constant cross-sectional area with respect to its length for achieving differential acceleration chromatographic separation of analytes. In another embodiment, the may have an increasing cross-sectional area with respect to its length for achieving differential acceleration chromatographic separation of analytes. The stationary phase precursor will ultimately be deposited to form a stationary phase within the tube.

In one embodiment, the chromatography columns made according to the above methods provide chromatographic resolution of analytes, compared to a conventional open tubular column, in about one-tenth the separation time.

The features, functions, and advantages that have been discussed can be achieved independently in various embodiments or may be combined in yet other embodiments, further details of which can be seen with reference to the following drawings and description.

DETAILED DESCRIPTION

Figure 1:
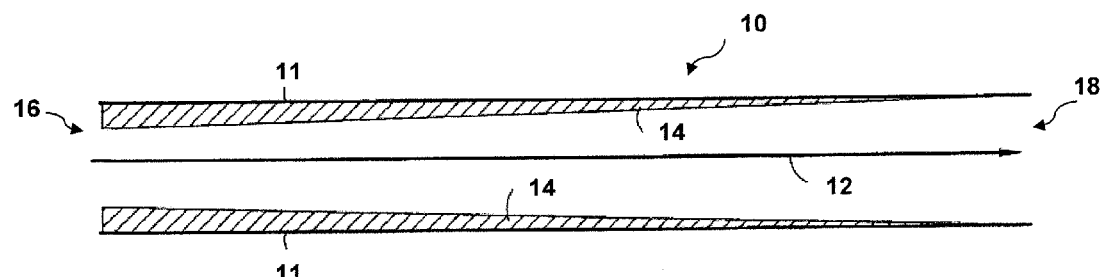
FIG. 1 is a side view of an embodiment of a column of a chromatographic system formed from a constant cross-sectional area tube and a gradually decreasing thickness of stationary phase therein.

Referring to FIG. 1, a side view illustration of a column, generally designated 10, of a chromatographic system having a variable stationary phase film thickness is illustrated. The column 10 includes a tube 11 (illustrated as a straight-walled tube, but is not limited thereto) having a mobile phase, designated by arrow 12, flowing from the inlet 16 of the tube 11 towards its outlet 18. The stationary phase 14 is deposited on the inner surface of tube 11 such that the stationary phase 14 is thicker at the inlet 16 and thinner at the outlet 18 and thins in a generally linearly manner therebetween. In the arrangement shown in FIG. 1, differential acceleration of the analyte is provided by the varied thickness of the stationary phase film 14.

The arrangement shown in FIG. 1 may be used for gas chromatography (GC). In this embodiment, the tubular, constant diameter tube 11 is easily available, robust, and compatible with existing gas chromatographs. For example, tube 11 can be a polyimide-protected, fused silica column with an undeactivated (native glass) or deactivated inner glass surface. In one embodiment, the stationary phase film 14 may be polydimethylsiloxane that may be doped with cross-linking agents that can be deposited in the tube 11 such that the film thickness decreases down the length of the column 10, ideally being as close to zero thickness as possible at outlet 18. Other suitable stationary phases are discussed below. The cross-sectional area and length of the tube 11, as well as starting stationary phase thickness, and the rate/function of film tapering, can vary depending upon the chromatography separation that will be performed therein. However, generally speaking in one case the inner diameter can be between 50 μm and 500 μm, the film thickness can range from 100-1000 nm at the inlet of the column and should be as close to zero at the end of the column as possible, and the length can be about 0.001 to 300 meters.

Figure 2:
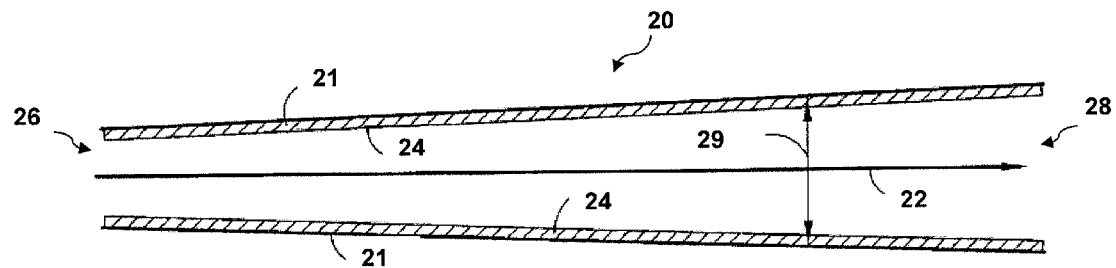
FIG. 2 is a side view of an embodiment of a column of a chromatographic system formed from a tube having a gradually enlarging cross-sectional area and a uniform thickness of stationary phase therein.

Referring now to FIG. 2, a side view of a column, generally designated 20, of a chromatographic system having variable inner diameter/variable cross-sectional area is illustrated. The column 20 includes a tube 21 having a mobile phase, designated by arrow 22, flowing from the inlet 26 of tube 11 towards its outlet 28. The stationary phase 24 is deposited as a constant thickness on the inner surface of the tube 21. In the arrangement shown in FIG. 2, differential acceleration is provided by the gradually enlarging cross-sectional area of the column 20 along its length. The enlarging cross-sectional area may enlarge in a generally linear manner as illustrated, but is not limited thereto. As shown, the cross-sectional area of column 20 is smaller at the inlet 26 and larger at the outlet 28 while having a uniform thickness of the stationary phase 24, such that the over all cross-sectional area of the column 20 varies steadily and gradually (generally linearly in one case) along the length of its interior.

In one embodiment, tubes 11 and 21 are not circular in cross-section, but are rectangular in cross-section. In this embodiment, the vertical dimension 29 of FIG. 2 is the width of tube 21. The width is varying, becoming larger in the direction of the outlet 28. The height of tube 21 (extending into and out of the page of FIG. 2) may remain constant throughout the length of tube 21 for ease of fabrication, but may vary similarly to the width if fabrication capabilities allow. Tube 21 is preferably coated with a stationary phase 24 of constant thickness. This approach would combine sources of differential acceleration through the expanding cross-sectional area and decreasing stationary phase thickness, yielding a greater degree of differential acceleration than with only a single source of acceleration.

Figure 3:
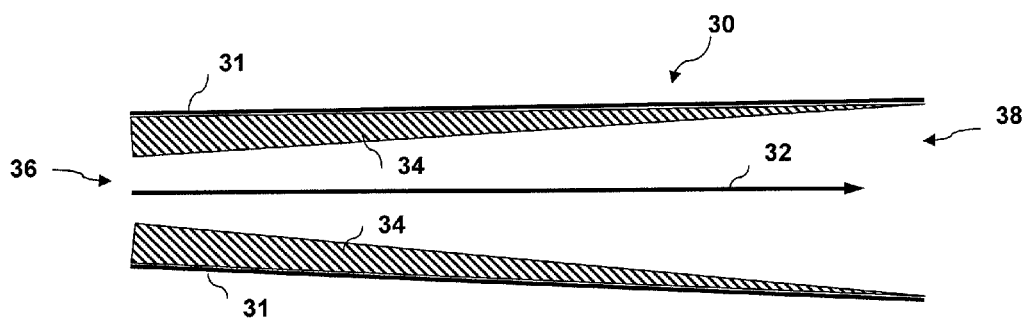
FIG. 3 is a side view of an embodiment of a column of a chromatographic system formed from a tube having a gradually enlarging cross-sectional area and a gradually reducing thickness of the stationary phase.

Now referring to FIG. 3, in one embodiment, a chromatography column, generally designated 30, having a variable stationary phase film thickness is illustrated. The column 30 includes a tube 31 having a gradually enlarging cross-sectional area that is narrower at the inlet 36 than at the outlet 38. A mobile phase, designated by arrow 32, may flow from the inlet 36 of the column towards the outlet 38. The stationary phase 34 is deposited on the inner surface of tube 31 such that the stationary phase 34 is thicker at the inlet 36 and thinner at the outlet 38 and thins in a generally linearly manner therebetween. In the arrangement shown in FIG. 3, differential acceleration is provided by the varied geometry provided by the combination of the tube 31 and the gradient of the stationary phase 34 thickness.

The gas chromatography columns referred to herein as a "column" or "tubular column" may be open tubular columns, but are not limited to circular cross-sectional areas. The columns may be circular, semi-circular, elliptical, toroidal, oval, square, rectangular, triangular, hexagonal, trapezoidal, parallelogram, or other geometric shapes in cross-sectional area. In another embodiment, the column may be a micro-gas chromatography column made using MEMS technology. Using MEMS technology, the column may be in the form of an etched wafer or monolithic chip, for example, as disclosed in U.S. Pat. No. 6,838,640 to Wise et al., which is incorporated herein in its entirety. It is well known in the art that various MEMS methods will create a variety of cross-sectional shapes in addition to those listed above.

Disclosed below are methods and apparatus for making VGCs such as those described above. The methods and apparatus enable the deposition of controlled film thickness gradients in both constant and variable cross-section OTCs as well as the deposition of constant film thicknesses in variable cross-section OTCs.

One example equation, Equation 1 below, demonstrates one way the deposited film thickness is governed by the coating parameters when using static stationary phase deposition:

$$t_f = r\left(1 - \sqrt{1 - \frac{c}{\rho}}\right) \cong r\frac{c}{2\rho} \tag{1}$$

where $t_f$ is the thickness of the stationary phase film, r is the radius of the un-coated tube (soon to be column), c is the concentration (mass/volume) of stationary phase dissolved in the coating liquid, and ρ is the density of the stationary phase in the precipitated or solid form. Compensation factors can be added to the c or ρ terms to account for changes to the deposited film during alteration steps as the OTC is conditioned.

Equation 1 makes clear that the thickness of the deposited stationary phase is directly proportional to the inner radius of the un-coated tube. Therefore, if one wishes to use traditional static coating methods to deposit a stationary phase on a tube with increasing cross-sectional area as a function of length, the resultant column would have a film thickness that increases in proportion to the radius of the column; in other words, the stationary phase will not have a constant thickness, and in fact may even have a thickness gradient reversed from that desired and thus would not exhibit differential acceleration (i.e. VGC behavior).

Another example equation, Equation 2 below, is presented that is the analog of equation 1 for rectangular tubes, that is it gives $t_f$ as follows:

$$t_f = \frac{(h+w) - \sqrt{(h+w)^2 + \frac{4hwc}{\rho}}}{4} \cong \frac{hwc}{2\rho(h+w)} \quad (2)$$

Where h is the height of the tube cross-section, w is the width of the tube cross-section, c the concentration of stationary phase precursor in the static coating solution, and ρ is the density of the deposited stationary phase film. Similarly to equation 1, equation 2 shows that the traditional static coating approach will generate a stationary phase of increasing film thickness with respect to column length if applied to a tube exhibiting the variable cross-section VGC approach.

Equations other than 1 and 2 are possible for other tubing cross-sections; however, because they behave similarly to equations 1 and 2, they are not discussed herein.

Figure 4:
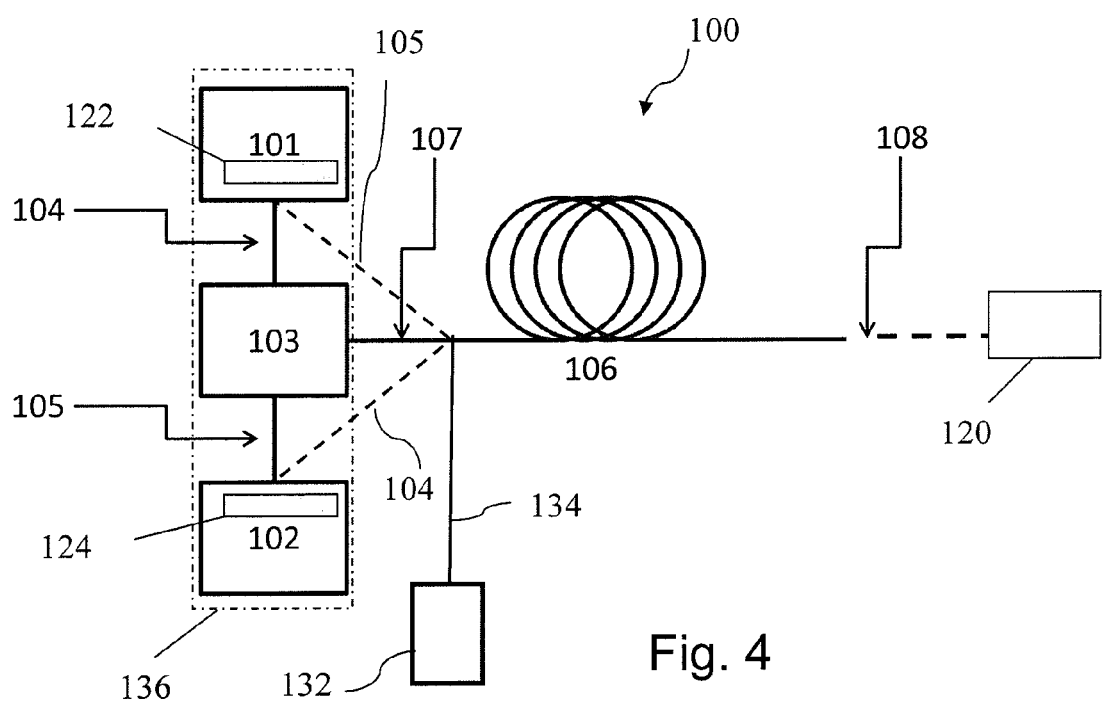
FIG. 4 is a schematic of an embodiment of a gradient preparation system for depositing a stationary phase thickness in an open tube.
Figure 6:
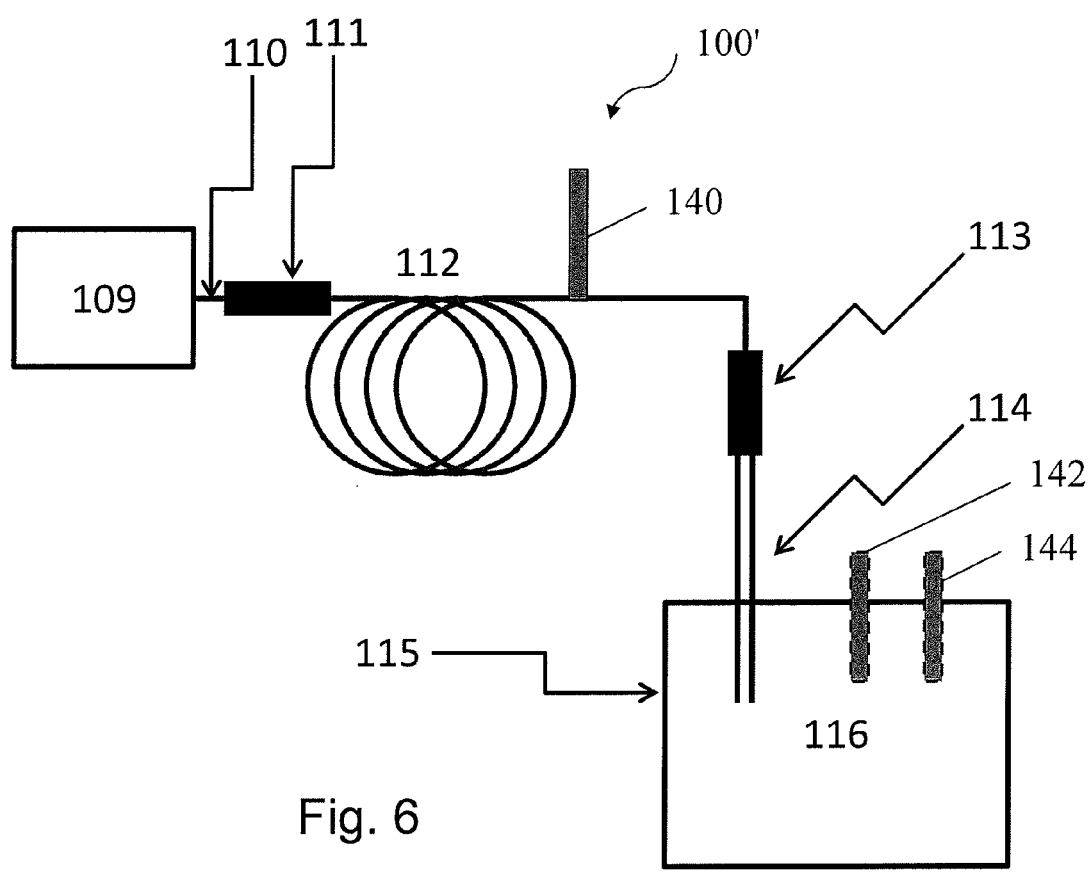
FIG. 6 is a schematic of another embodiment of a gradient preparation system for depositing a stationary phase thickness in an open tube.

The methods and apparatus disclosed below can result in a tube with a stationary phase therein providing a chromatography column with a gradually enlarging cross-sectional area. Different apparatus for providing such columns are depicted in FIGS. 4 and 6, generally designated 100 and 100' respectively. Each apparatus will be described in detail below.

Figure 13:
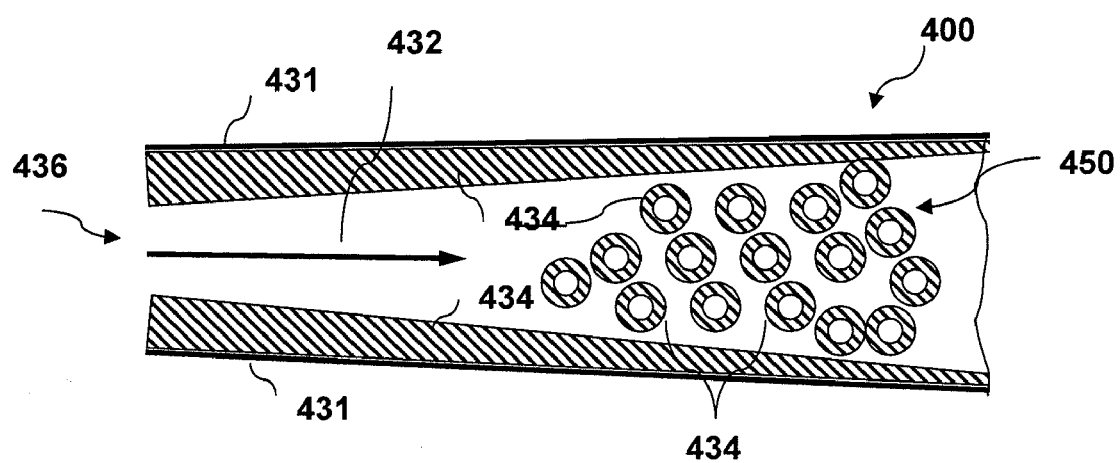
FIG. 13 is a side view of a portion of a column similar that of FIG. 3 with surface area-increasing member within the tube.

Referring now to FIG. 13, in another embodiment, a chromatography column, generally designated as 400, having a variable stationary phase film thickness is illustrated. The column 400 includes a tube 431 having a gradually enlarging cross-sectional area that is narrower at the inlet 436 than toward the outlet (not shown). As illustrated, tube 431 includes surface area-increasing members 450 therein that have stationary phase precursor deposited thereon as well as on the inner surface of the tube 431 such that there is a greater thickness of stationary phase precursor in the stationary phase 434 nearest the inlet which decreases toward the outlet. A mobile phase, designated by arrow 432, may flow from the inlet 436 of the column towards the outlet with differential acceleration provided by the varied geometry provided by the combination of the tube 431 and the gradient of the stationary phase 434. The surface are-increasing members may be particles or fibers such as glass fibers packed within the tube 106.

Similarly to a particle-packed column, other structures can be included in the tube 106 flow path to increase surface area, increase sample capacity (cross-sectional area of stationary phase), decrease the average diffusion distance for analyte molecules to reach the stationary phase (i.e. increasing column efficiency) or similar. In one embodiment, the tube 106 may be micromachined to have various pathways therethrough. The pathways may provide additional surface area for deposition of the stationary phase precursor for formation of the gradient of the stationary phase discussed above. Micromachined silicon columns containing pillars that provide larger sample capacity with better chromatographic efficiency without increasing pressure restriction have recently been reported (T. Nakai et al, "Micro-fabricated semi-packed column for gas chromatography by using functionalized parylene as a stationary phase, *J. Micromech. Microeng.*, 2009, 19(6), 065032). The concentration gradient of the stationary phase precursor to be introduced into the tube 106 is determined from the desired film thickness profile and appropriate equation.

The stationary phase precursor may be dissolved, suspended, dispersed, or otherwise carried in an appropriate solvent or other carrier phase. In one embodiment, the stationary phase precursor may be polydimethyl siloxane (PDMS) and the solvent may be n-pentane, dichloromethane, 1,2-dichloroethane, benzene, or similar solvent, or a mixture of these or similar solvents. Other suitable stationary phase precursors include, but are not limited to, polyethylene glycol (PEG), polydiphenyl siloxane (PDPS), polyditrifluoropropyl siloxane. Other suitable solvents include, but are not limited to, volatile solvents such as n-pentane, dichloromethane, 1,2-dichloroethane, benzene, or similar solvent, or a mixture of these or similar solvents Referring now to FIG. 4, apparatus 100 is generally a mechanism for introducing various concentrations of stationary phase precursor in an appropriately volatile solvent into a tube 106. In one embodiment, the tube 106 may be un-coated. Apparatus 100 includes two or more flow devices 101, 102 capable of delivering appropriate volumes of fluids 122, 124 to the tube 106. The fluids 122, 124 may contain an appropriate concentration of solute and/or a solvent, wherein the solute is typically the stationary phase precursor. The flow devices 122, 124 are each connected to the tube 106 by separate tubes 104, 105, respectively, via a junction 103 or via a direct connection to the mouth of the tube itself. In the embodiment providing a junction 103, junction 103 connects the flow devices 101, 102 to tube 106. In one embodiment, tube 106 is directly fluidly connected to the junction 103. However, as illustrated in FIG. 3, if desired tubing 107 can be used to join the tube 106 to the junction 103. If tubing 107 is used, proper precautions should be taken to account for delays and variations in volume (as discussed above in reference to Equations 1 and 2) that tubing 107 may introduce. Apparatus 100 may optionally include another component 120 such as a waste reservoir, a flow switch or valve, a flow meter, or any other useful fluidic device, a vacuum pump, or combinations thereof connected to the outlet 108 of tube 106.

Ultimately, the fluids 122, 124 from the flow devices 101, 102 are delivered to the tube 106 as a mixture or are simultaneously delivered to the mouth of the tube where they become mixed. The mixing of the first and second fluids 122, 124 is a function of the time and volume to fill the tube 106 with the appropriate stationary phase concentration gradient profile. With respect to the fluids 122, 124, at least one should comprise the stationary phase precursor that will be used to prepare the stationary phase. The stationary phase precursor is carried in an appropriate solvent such as a volatile solvent. The other fluid may be pure solvent. Either of the fluids 122, 124 may contain a reagent for cross-linking of stationary phase, a deactivation agent, other useful chemical components, and combinations thereof. For further detail relating to cross-linking agents, cross-linking and stationary phase deposition, see Anal. Chem. 2004, 76(9), 2629-2637; and Anal. Chem. 2006, 78(8), 2623-2630 which are both incorporated by reference herein.

In one embodiment, the first and second flow devices 101, 102 may take the form of or include syringe pumps and syringes for housing the first and second fluids 122, 124. In another embodiment, the first and second flow devices 101, 102 may each take the form of or include a high-pressure liquid chromatography (HPLC) pump. Alternately or in addition to the syring pumps and HPLC pump(s), the flow devices may include a peristaltic pump, a gravity feed device, or other fluid discharging devices. The flow devices 101, 102 may be controlled by a processor programmed to depress the plungers of the syringes or otherwise dispense the fluids at desired flow rates to create the concentration gradient of the stationary phase precursor within the tube 106. The processor may be a computer, microcontroller, data acquisition card controlled by a PC and software program, or similar. In another embodiment, the first and/or the second flow devices 101, 102 may include a pressure driven reservoir, a shrinking bottle, a HPLC pump, an ion chromatography pump, or other similar flow device. It should be appreciated that the first flow device 101 dispenses the first fluid 122 and that the second flow device 102 dispenses the second fluid 124, but there is no requirement that these be housed in/on separate apparatus. It is possible for a single apparatus to includes one or more fluid flow devices 101, 102 that are operable independent of one another to drive the dispensing of the first and second fluids 122, 124 at the desired rates. Alternately, as shown by the optional box 136 enclosing the fluid flow devices 101, 102 and mixing device 103, one apparatus may includes these components. In an additional embodiment, the multiple flow sources are integrated within a single pumping system, such as a gradient elution HPLC pump.

The length and cross-sectional area of the tubes 104, 105 connecting the flow sources 101, 102 to the junction 103 may be kept small relative to the volume of fluid flowing therethrough to minimize their impact upon errors in the concentration gradient that will be prepared within the tube 106. The internal volume and fluidic connections of the junction 103 are also kept to a minimum for the same reason. Alternatively, if the volumes of the tubing 104, 105 and junction 103 are relatively large, but of a known value, correction schemes can be employed to account for delays and dilution to still deliver a desired concentration of the stationary phase precursor to the tube. It is possible to back-calculate these volume and delay errors by comparing chromatographic retention factors of columns coated using apparatus 100 to columns coated with conventional static coating techniques using the same first and second fluids 122, 124 in known proportions.

Figure 5:
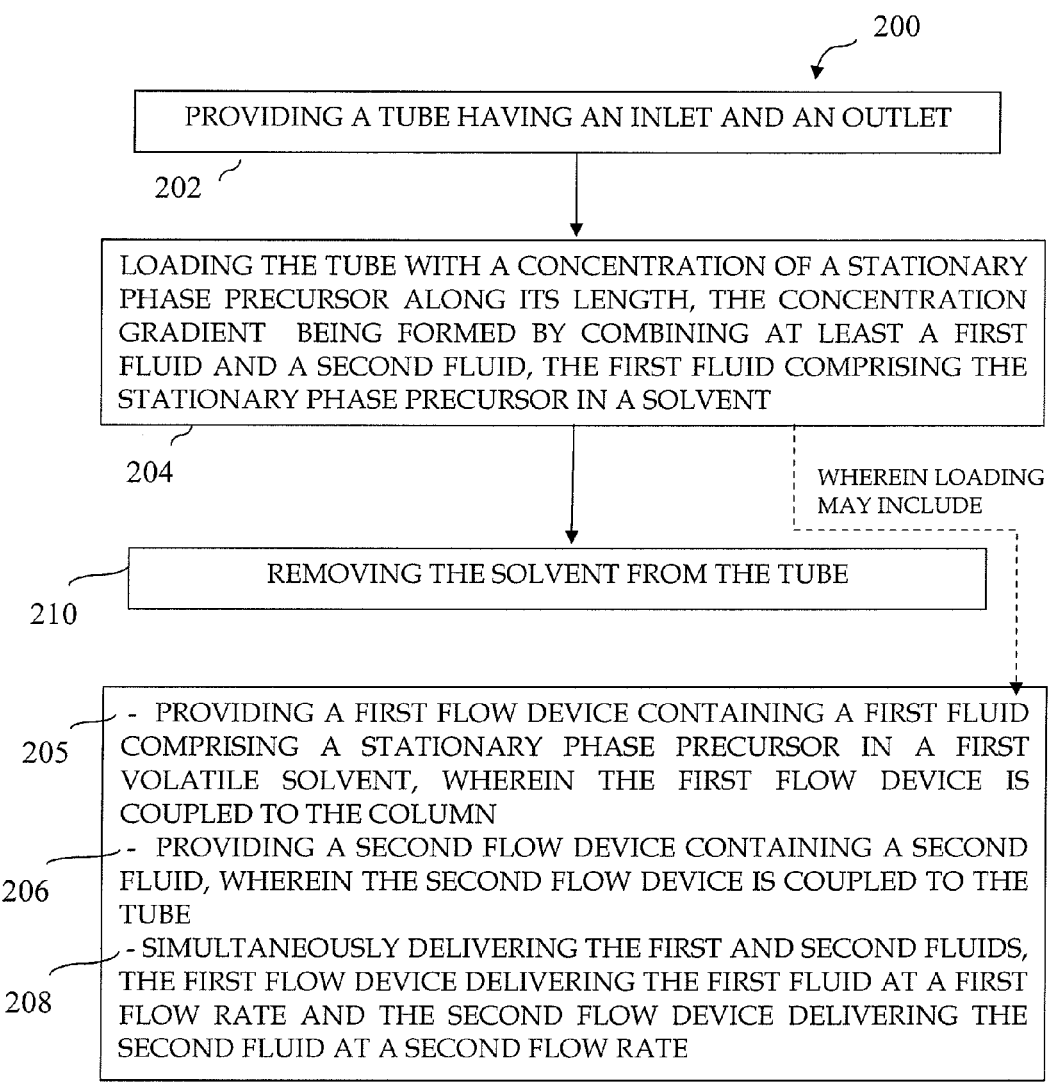
FIG. 5 is a flow chart of an embodiment of a method of depositing the stationary phase using an apparatus similar to that illustrated in FIG. 3.

Using an embodiment of the apparatus 100, a method 200 of depositing a stationary phase to provide a variable geometry column, generally depicted in FIG. 5, can be carried out. The method 200 includes a step 202 of providing a tube 106 having an inlet and an outlet. Then, step 204 includes loading the tube 106 with a concentration of a stationary phase precursor along its length. The concentration gradient is formed by combining at least a first fluid 122 and a second fluid 124. The first fluid 122 includes the stationary phase precursor in a solvent. Method 200 also includes step 210 where the solvent is removed from the tube to form the chromatography column.

The loading step 204 may include steps 205, 206, and 208. Step 205 includes providing a first flow device 101 containing a first fluid 122 comprising the stationary phase precursor in a first solvent. The first flow device 101 being fluidly coupled tube 106. Step 206 includes providing a second flow device 102 containing a second fluid 124. The second flow device 102 being fluidly coupled to the inlet of the tube 106. Step 208 involves simultaneously delivering the first and second fluids 122, 124 into tube 106 for a period of time to fill the tube.

At step 208 the delivery of the first and second fluids 122, 124 includes delivering the first fluid at a first flow rate and delivering the second fluid at a second flow rate, which are different flow rates and which both vary over the time period of filling the tube such that a concentration gradient of the stationary phase precursor is developed along the length of the tube. In one embodiment, the first and second flow rates vary over time while the combined first and second flow rates remains generally constant. In another embodiment, the first and second flow rates vary over time while the combined first and second flow rates vary.

In one embodiment, the first flow rate differs from the second flow rate, where one flow starts at minimum and increases with time to a maximum flow while the other starts at a maximum and decreases with time to a minimum. The value of the maximum flow depends on the tube's cross-section profile, length, and the desired time required to fill the tube prior to solvent removal. In one embodiment, the value for the minimum flow is zero; however, other minimum flow rates may be desirable in other scenarios (for example, if the target minimum stationary phase thickness is something other than zero). It is possible, but not necessary, that the maximum and minimum flow rates for the different flow sources be the same. Depending upon the length of the VGC, it may take about 3 seconds to about 2 min to fill the tube with the stationary phase precursor using the methods disclosed herein. Longer time periods are possible, but not generally necessary with most programmable flow sources such as the syringe pumps in the above embodiment.

In one embodiment, the first fluid has a higher concentration of stationary phase precursor relative to the second fluid and it is desired to deposit the stationary phase film thicker at the inlet of the column. Accordingly, the first flow rate will be higher than the second flow rate at the beginning of the delivering step 208. In order to create a concentration gradient of the stationary phase precursor along the interior length of the column, as the flow rate of the first fluid decreases the flow rate of the second fluid will increase proportionally thereby creating a lower concentration of precursor in the mixture of the two fluids—yielding a thinner stationary phase film once the deposition process is completed. During the delivery of the stationary phase precursor, there may be a point where the first and second flow rate are equal and thereafter the second flow rate will be higher than the first flow rate such that even lower concentrations of the stationary phase precursor are created.

In another embodiment, the second flow rate may initially be faster than the first flow rate and the process above is simply reversed.

In one embodiment, the first fluid contains at least a stationary phase precursor while the second fluid remains pure (i.e. a pure volatile solvent). In this embodiment, a first end of the tube (or both the first end and a second end of a tube) is intentionally filled with just the second fluid (pure volatile solvent) to create a known length of uncoated column before and/or after the coated region containing the stationary phase. This embodiment is similar to the common chromatographic practice of using a guard column on either end of an analytical column; except in this embodiment the "guard column" is integral to the analytical column which simplifies the configuration for end users and eliminates potential problems with a fluidic junction between the analytical and guard columns. A portion of uncoated first end of the tube (or of both the uncoated first end and second end) may be removed prior to use, as is the customary practice in chromatography, especially gas chromatography.

The method 200 may also include the step 210 of removing the solvent from the tube 106, such that the precursor is separated from the solvent and deposited on the walls of the tube. This includes, but is not limited to, evaporation of a volatile solvent. The solvent removal step 210 may be accomplished using known techniques from conventional static coating procedures. When the solvent is removed the stationary phase precursor is left behind as a stationary phase film or coating on the interior surface of the tube and thereby forms a chromatography column. The stationary phase will have a thickness $t_f$ as a function of column length in accordance with Equations 1 and 2 and the ideals of VGC/differential acceleration. The method 200 may include other steps known in conventional static coating procedures for chromatography column preparation such as drying of the stationary phase, conditioning and/or cross linking of the stationary phase, post treating the stationary phase for deactivation or functionalization. In one embodiment, the outlet 108 of the tube 106, as shown in FIG. 4 is connected to a valve and vacuum pump 120 such that immediately after the tube 106 is filled with the desired concentration gradient, the evaporation process begins. This approach minimizes evaporation from the end of the tube and therefore reduces risk of forming bubbles at either end of the tube 106 during evaporation. The evaporation process may be stopped before solvent is evaporated from the connections to the flow devices 101, 102 but after evaporation of all liquid in the tube 106 has been completed.

Referring again to FIG. 4, the apparatus 100 may also include a third flow device 132 connected by tubing 134 to the end of tube 106 that is opposite the outlet 108 where the solvent removal will occur. For example, if evaporation by a pump such as a vacuum pump is occurring, then the third flow device 132 is connected to the end opposite the vacuum pump. The third flow device 132 is used to manipulate remaining liquid during the solvent removal step 210 of process 200. As the solvent-gas interface (meniscus) retreats, leaving behind stationary phase precursor, the flow device can be used to pull the liquid backwards resulting in less stationary phase precursor being deposited than dictated by the traditional static coating theory (equations 1 and 2).

Figure 14:
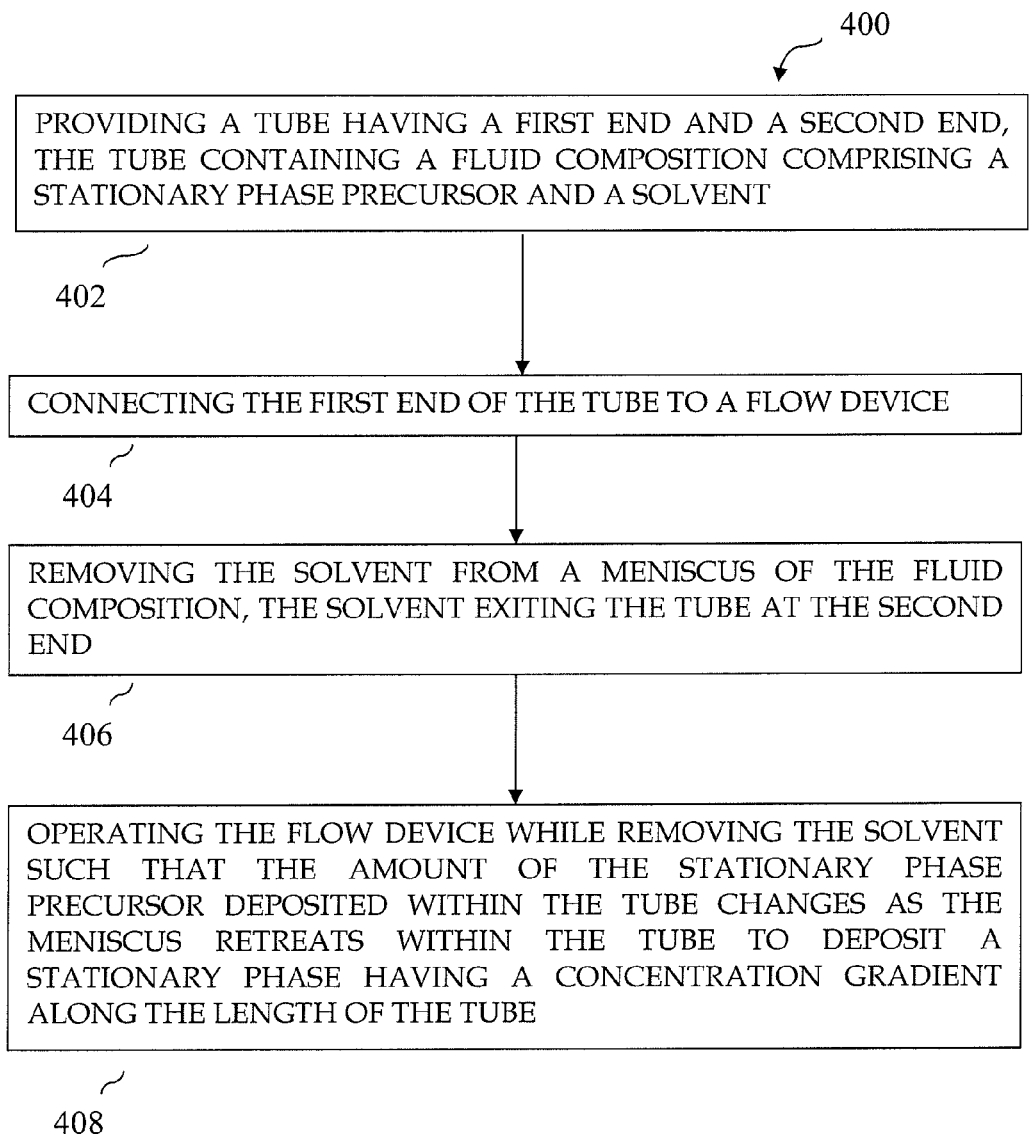
FIG. 14 is a flow chart of an embodiment of a method of depositing a stationary phase in a tube to produce a VGC.

Referring now to FIG. 14 and FIG. 4, in another embodiment, the third flow device 132 in combination with the solvent removal may be used to create a stationary phase concentration gradient in a tube similar to tube 106. In this method, generally designated as 400 in FIG. 14, the first step 402 includes providing a tube similar to tube 106 that is filled with a fluid comprising a stationary phase precursor at one predetermined concentration. Then, in step 404, one end of the tube 106 is connected to a flow device, similar to the third flow device 132 in FIG. 4, and the other end is available for the solvent to exit the tube. The solvent is removed in step 406. The solvent is removed from the meniscus of the fluid composition by operating the flow device to perform step 408. In step 408, as the solvent is being removed to deposit the stationary phase precursor, the third flow device 132 is operated such that the amount of the stationary phase precursor deposited within the tube changes as the meniscus retreats within the tube to deposit a stationary phase having a concentration gradient along the length of the tube. In one embodiment, the third flow device pulls the fluid, at a changing rate, away from the end of the tube where the solvent removal is occurring to change the amount of stationary phase precursor coating the interior of the tube. This method can be used to create VGCs similar to those described above and shown in FIGS. 1-3.

Referring now to FIG. 6, apparatus 100', for introducing a stationary phase onto the inner surface of a tube 112, sometimes referred to as an open tubular column, is illustrated. Apparatus 100' employs an electrochemical reaction at the inner surface of the tube 112 to deposit the stationary phase according to the desired film thickness profile (referred to herein as the electroplated stationary phase). In one embodiment, the tube 112 is a stainless steel chromatographic capillary column. An "iR" drop, that is a drop in electrical potential as a result of resistance to charge movement through a solution, may be used to restrict an electrochemical reaction as a function of length down the tube 112. In one embodiment, the IR drop is used to electroplate one end of the tube with a thicker layer of stationary phase than the other end. The thickness of the stationary phase may decrease gradually (generally linearly) from one end of the tube to the other. Tube 112 may have a generally constant cross-sectional area, or a generally enlarging cross-sectional area (gradually or non-gradually enlarging). Regardless of which type of tube 112 used, the resulting column with the stationary phase therein, starting from the inlet of the column, has a generally decreasing chromatographic phase ratio or generally decreasing retention factor from one end thereof to the other. In another embodiment, the iR drop may be controlled to electroplate the tube with a uniform film thickness of the stationary phase.

Apparatus 100' includes an tube 112 having an electrically conductive interior surface that is filled with a composition including an aqueous supporting electrolyte such as NaOH, HCl, NaCl, or the like and a dilute stationary phase precursor such as phenol or the like, and other additives such as stabilizers, cross-linkers, or other preparatory reagents. Within tube 112, the aqueous electrolyte is present in a concentration sufficient to conduct charge at the rate necessary for the electrochemical reaction forming the electroplated stationary phase.

Alternatively, a multi-step reaction can be carried out that is initiated by a reactant precursor that undergoes an electrochemical reaction at the interior of the tube 112. This includes, but is not limited, to an acid catalyzed sol-gel process where acid or hydrogen ions are generated electrochemically at the interior of the tube 112 from a reactant precursor, which then catalyzes a sol-gel formed stationary phase. In another embodiment, the reactant precursor may be a sol-gel precursor. Suitable sol-gel precursors that may be applicable here include water and those disclosed in U.S. Pat. No. 6,783, 680 to Malik and WO/2002/072225 to Malik et al.

The apparatus 100' also includes a voltage source 140, such as a potentiostat or the like, connected to the tube 112, in particular electrically connected to the electrically conductive interior surface of the tube. The voltage source 140 may be wired, clipped, or the like to the interior surface of the tube 112. Also connected to tube 112 is a reservoir 115 of an aqueous electrolyte that is in fluid communication with at least one end of the tube 112. The reservoir 115 may include an aqueous electrolyte 116 such as KCl at a concentration sufficient to conduct charge at the necessary rate and optionally any other reagent included in the composition within the tube 112. The reservoir 115 may also include additional electrochemical devices such as an auxiliary or counter electrode 142 and a reference electrode 144 for controlling or monitoring the electrochemical reactions.

In one embodiment, an electrically insulating union 113 and tube 114 connect the end of the tube 112 to the reservoir 115. The electrically insulating tube 114 prevents electrochemical plating at the end and outer surface of the tube 112 with stationary phase and insures that all current passed through electrochemical reactions are due to stationary phase being deposited on the inside of the tube 112. This should also allow improved accuracy if using Faradaic charge to estimate the film thickness profile.

In another embodiment, apparatus 100' includes an additional reservoir 109 connected to the opposite end of the tube 112 in fluid communication with the composition therein. The reservoir 109 may contain a reserve of the composition filling the tube 112. The reservoir 109 may be connected to the tube by a connection tube 110 and insulating union 111. The reservoir 109 may provide a means of flushing the tube 112 with the composition filling the tube 112, which includes the stationary phase precursor, to ensure that solvent is not lost to evaporation, or to ensure that the entire tube 112 is filled uniformly before the electroplating process begins.

A variety of electrochemical waveforms can be used to drive a variety of electrochemical reactions that result in the formation of an insoluble film or films that can be employed as chromatographic stationary phases. In one embodiment, repeated cyclic voltammograms (CV) are used to react the composition within the tube 112 forming the electroplated stationary phase. In a composition comprising 5 mM phenol in 25 M NaOH the cyclic voltammograms produce an electrochemical reaction converting the phenol into a polyphenol stationary phase (-phenyl-O—), which has excellent high temperature stability in both inert and oxygen-containing carrier gases. Each sequential CV drives more electrochemical reactions which results in more deposited polyphenol stationary phase. However, a maximum thickness may exist due to passivation of the inner surface (i.e. electrode surface), but in other scenarios surface defects permit sequential layers of polyphenol to be coated on top of each other.

Figure 7:
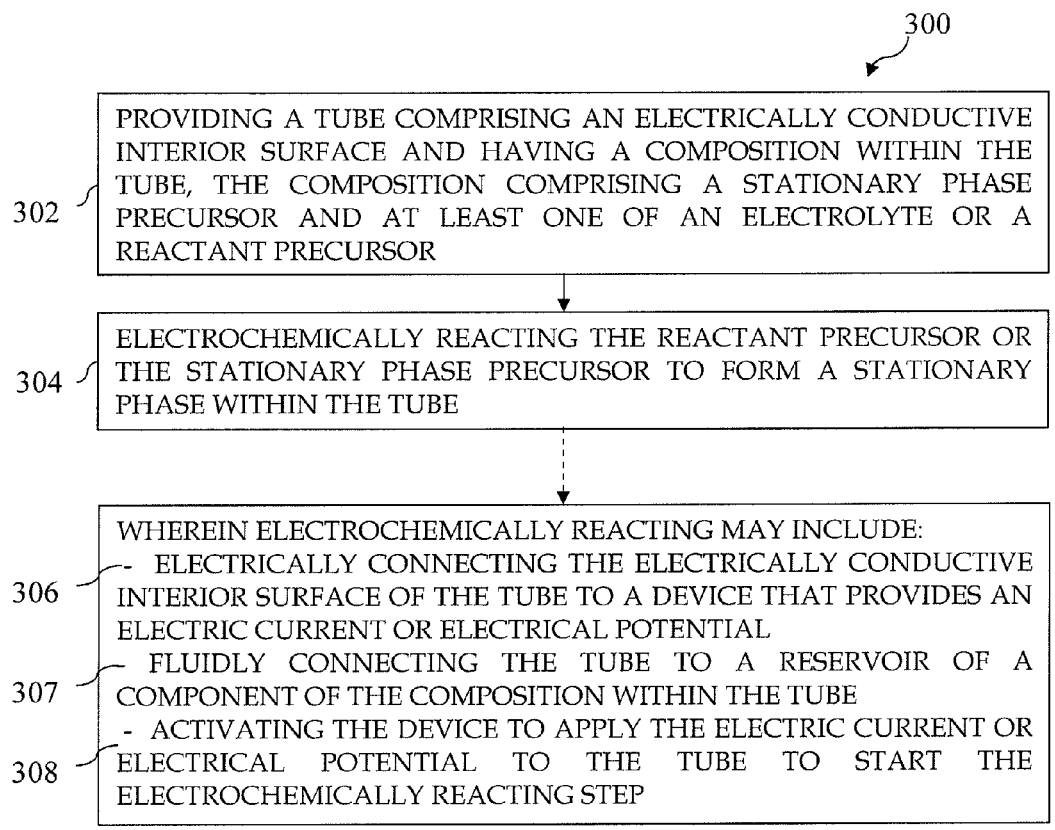
FIG. 7 is a flow chart of an embodiment of a method of depositing a stationary phase using an apparatus similar to that illustrated in FIG. 5.

Using an embodiment of the apparatus 100', a method 300 of depositing a stationary phase to provide a variable geometry column, generally depicted in FIG. 7, can be carried out. The method 300 includes, a step 302, providing a tube 112 having an electrically conductive interior surface and having a composition within the tube. The tube may be substantially filled with a composition comprising a stationary phase precursor and at least one of an electrolyte or a reactant precursor. Then, step 304 includes electrochemically reacting the reactant precursor or the stationary phase precursor to form a stationary phase within the tube.

Step 304 may include multiple steps 306, 307, and 308. Step 306 includes electrically connecting the electrically conductive interior surface of the tube to a device that provides an electric current or electric potential. Step 307 includes fluidly connecting one end of the tube 112 to a reservoir 115 of a component of the composition within the tube. Step 308 includes activating the device 140 to apply the electric current or electrical potential to the tube 112 to start the electrochemical reaction step 304. In one embodiment, the component of the composition housed within the reservoir 115 is an electrolyte 116. In one embodiment, the electrolyte 116 may be an aqueous electrolyte. The electric current causes an electrochemical reaction that ultimately deposits stationary phase on the interior of the tube 112 wherein the composition provides an electrical resistance that restricts the electrochemical reaction of the stationary phase precursor as a function of the length of the column to form a deposition gradient of the stationary phase therein.

In one embodiment, the method may also include a step of connecting the opposite end of tube 112 to a reservoir 109 of the composition that fills the tube. The tube 112 may be connected to the reservoir 109 in an empty state such that the method may also include the step of filling the tube 112 with the composition from the reservoir 109.

Figure 9:
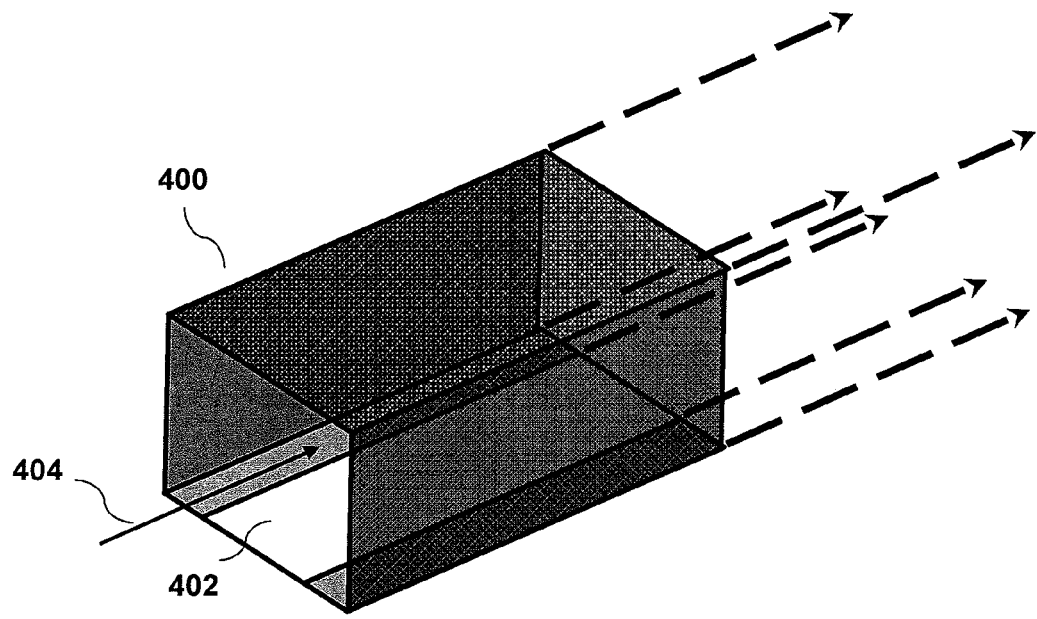
FIG. 9 is side perspective view of a portion of a tube having a generally rectangular cross-sectional area and having a conductive surface down the length of the tube for making VGCs.

In other embodiments, the natural "iR" drop of the tube may be altered to achieve a stationary phase with a more constant profile as a function of tube length. Many methods are clearly possible, one such method, as shown in FIG. 9, would be to create a second conductive surface 402 down the length of a tube 400 (a small portion of which is shown), such that it is electrically insulated from the rest of the tube and can serve as the counter electrode. Arrow 404 designates the direction of movement of a mobile phase. In effect, this rearranges the "iR" drop such that it is perpendicular to the length of the tube and thereby does not cause a change in the stationary phase profile along the length of the column.

Figure 8:
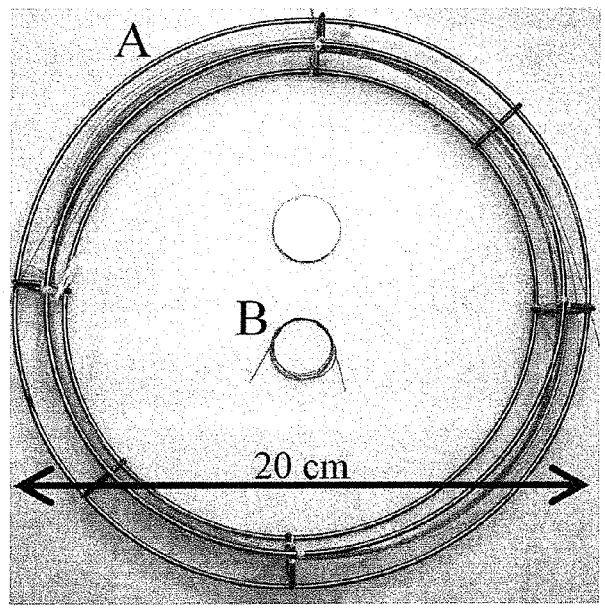
FIG. 8 is a photograph of a conventional chromatography column and a VGC prepared using one of the methods and apparatus disclosed herein for size comparison.

As seen in FIG. 8, a conventional high-speed gas chromatography column A (a 10 mm, 100 µm ID, column) is significantly longer than column B, a VGC, made by the methods disclosed herein. The variable geometry column B is about twenty times shorter in length than column A. In one embodiment, the VGC may be about 0.1 inches to about 4000 inches in length. In another embodiment, the VGC may be about 1 inch to about 40 inches in length. In yet another embodiment, the VGC may be about 40 inches to 400 inches in length.

Several examples of VGCs are presented below along with experimental data demonstrating several aspects of each individual column. For all cases a commercial laboratory-grade GC (7890A, Agilent Technologies, Inc., Santa Clara, Calif., USA) was used for the column evaluation. The instrument features a conventional 8-sample automatic liquid sampler capable of injecting 0.02 µL liquid aliquots into the split/splitless inlet of the instrument. To achieve injections that were as small as possible to allow operation with low band-broadening columns (i.e. maintain injections that do not significantly add to the extra-column band broadening), a gas injection was provided consisting of a mixture of methane gas and n-alkane vapors. By eliminating the evaporation of a liquid sample (500-1000 fold increase in volume), the split injector is able to provide much smaller injection plugs, and therefore allow accurate evaluation of shorter/faster column configurations. In all cases, the split ratio was adjusted down (i.e. larger injection plug) and the peak width measured to ensure the injection pulse was small with respect to the on-column band broadening. After evaluation, the data was processed using Grams 32/AI software from ThermoFisher Scientific (Waltham, Mass., USA). Data processing included extraction of the full width at half height (parallel to baseline). Full width at half height is assumed to be 2.354σ (σ being the standard deviation of the Gaussian distribution). As is conventional in chromatography, full baseline width of a chromatographic peak is assumed to be 4σ (95.44% of the integrated area of the Gaussian distribution).

Example 1

Trial 1

A conventional high-speed gas chromatography column of 50 cm length, 100 µm internal diameter, and having a 400 nm thick non-polar stationary phase of polydimethylsiloxane (Restek, Bellefonte, Pa., USA) was compared against a VGC prepared using an apparatus similar to that illustrated in FIG. 3 and described above. The VGC was formed from a fused silica capillary column of 50 cm with a 100 µm constant internal diameter and intermediate polarity deactivation (Restek, Bellefonte, Pa., USA). A non-polar stationary phase of polydimethylsiloxane was deposited therein at a variable thickness along the internal diameter thereof with a maximum thickness of 400 nm at the inlet gradually (generally linearly) decreasing to a thickness of 0 nm at the outlet.

Figure 10:
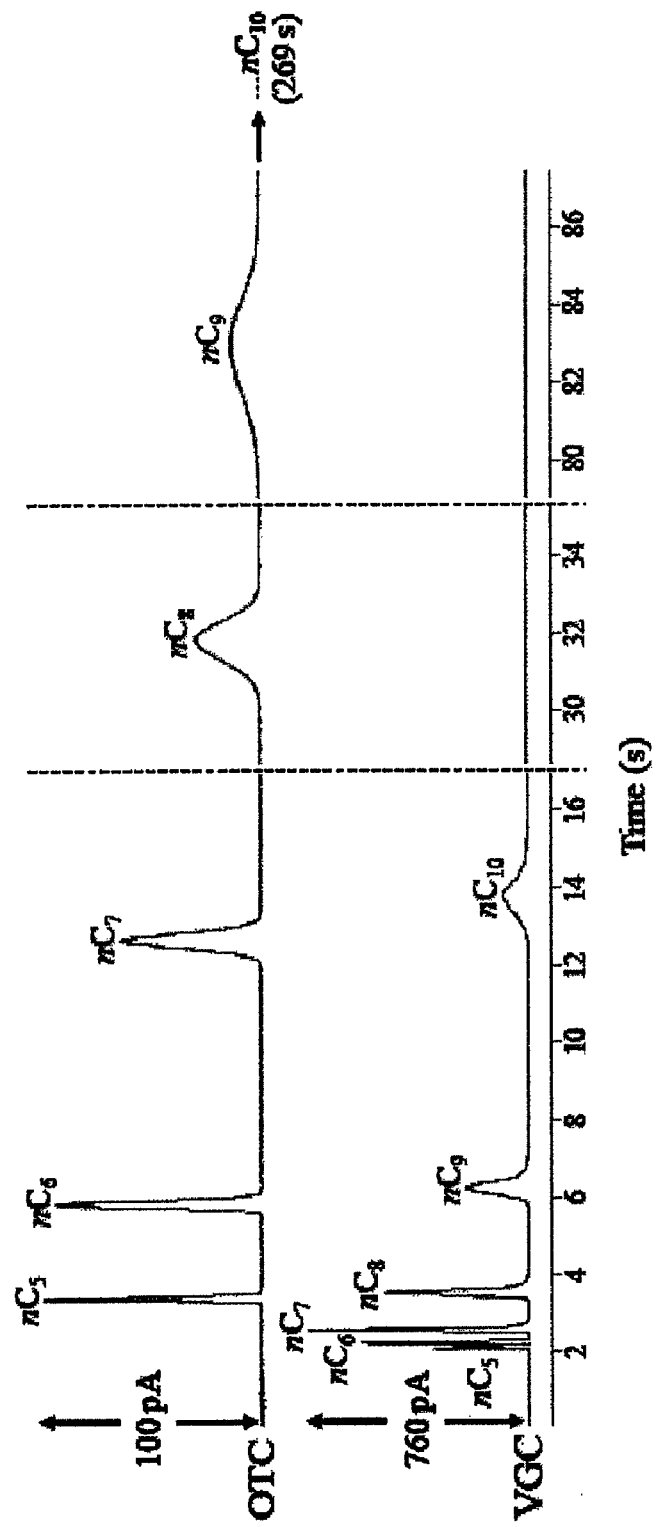
FIG. 10 contains two gas chromatograms, the top chromatogram being from a conventional open tubular column and the bottom chromatograph being from a VGC prepared using one of the methods and apparatus disclosed herein.

Both the VGC and the conventional column were operated under the same carrier gas flow rate and oven temperatures in a conventional gas chromatograph with hydrogen as the carrier gas and a flame ionization detector on the column outlet. The gas chromatograms from Trial 1 carried out at 3 psi $H_2$ carrier gas at 26° C. to separate a diagnostic mixture of $C_5$ to $C_{10}$ n-alkanes are shown in FIG. 10.

The VGC separated the $C_5$ to $C_{10}$ n-alkanes in less than 14 seconds with a n-heptane peak of 760 pA whereas the conventional column required almost 4.5 minutes and only had a n-heptane peak of 75 pA. This data shows that the VGC, while being a comparable size to the conventional column, produces high quality resolution of the hydrocarbons in one-tenth the time and with as much as a 10-fold improvement in detectability (pA).

Trial 2

A critical aspect to the proof of concept for the methods disclosed herein is to demonstrate that the stationary phase thickness gradient is indeed created as intended. The simplest experiment for proving this is to evaluate a single gas chromatography column in a GC under first forward flow conditions and then reverse flow conditions. Then, the forward and reverse results are compared. For a standard chromatography column (i.e., a non-VGC), the forward and reverse chromatograms will be the same. On the contrary, the forward and reverse chromatograms of a VGC will be significantly different.

To do this, a 50 cm long fused silica tube (Restek, Bellefonte, Pa., USA), with 100 μm inner diameter and intermediate polarity inner surface deactivation was coated with polydimethylsiloxane as described above using apparatus 100. The concentration gradient was prepared such that a 400 nm stationary phase film was deposited at the inlet to the column, which tapered down to zero thickness at the outlet of the column.

Figure 11:
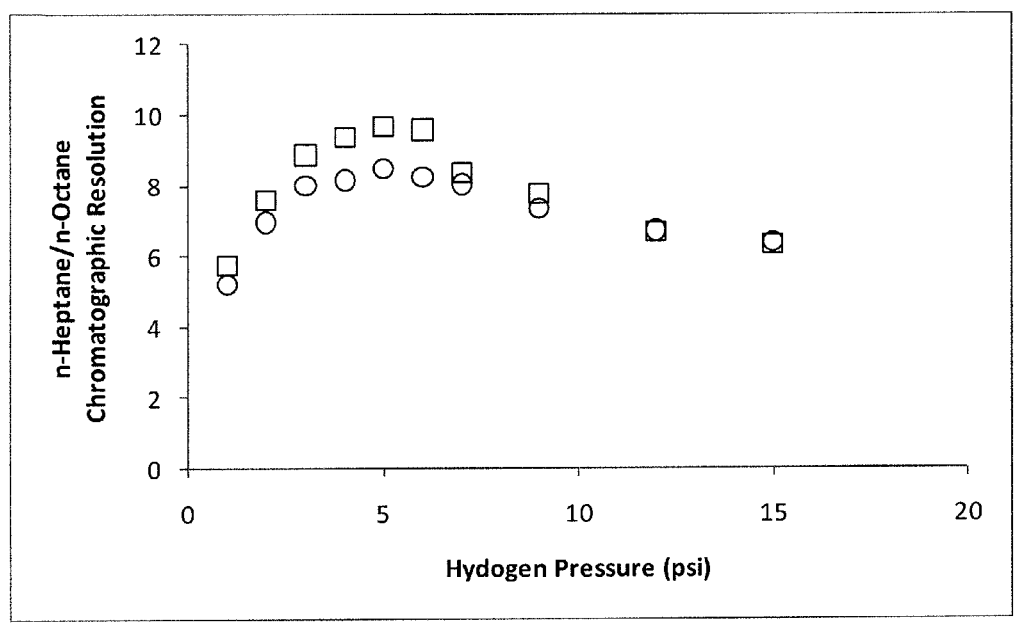
FIG. 11 is a chromatographic resolution versus inlet pressure plot for the n-heptane/n-octane peak pair separated on a VGC operated in forward (squares) and reverse (circles) flow.

The column was installed in the GC and a gas phase, analyte sample mixture consisting of methane, n-pentane, n-hexane, n-heptane, n-octane, n-nonane, and n-decane were separated under a series of different inlet pressures. Conventionally, chromatographers then calculate the number of theoretical plates for each component and plot against the average column linear velocity (calculated from the methane retention time), forming what is known in the art as a Golay plot. Herein, the approach is from a chromatographic resolution perspective, since enhanced separation between adjacent components is the primary advantage of the methods and resulting columns disclosed, plotted against inlet pressure rather than flow rate. Chromatographic resolution is the difference in retention time between two components divided by the average full baseline peak width of the two components (as defined above). Higher flow rates are achieved through higher inlet pressures; however, the relationship between the two is not always a linear function. The chromatographic resolution versus inlet pressure plot for the n-heptane/n-octane peak pair is shown in FIG. 11 for both the forward (square) and reverse (circles) flow directions. At high and low inlet pressure, the two flow directions appear to produce nearly identical separation performance because band broadening masks the advantages of differential acceleration; however, from 3 to 8 psi, the forward flow direction produces significantly better chromatographic resolution than the reverse direction because of the advantages from differential acceleration. With a conventional OTC, these forward and reverse flow plots are always identical because the stationary phase profile is constant along the length of the column.

Example 2

Figure 12:
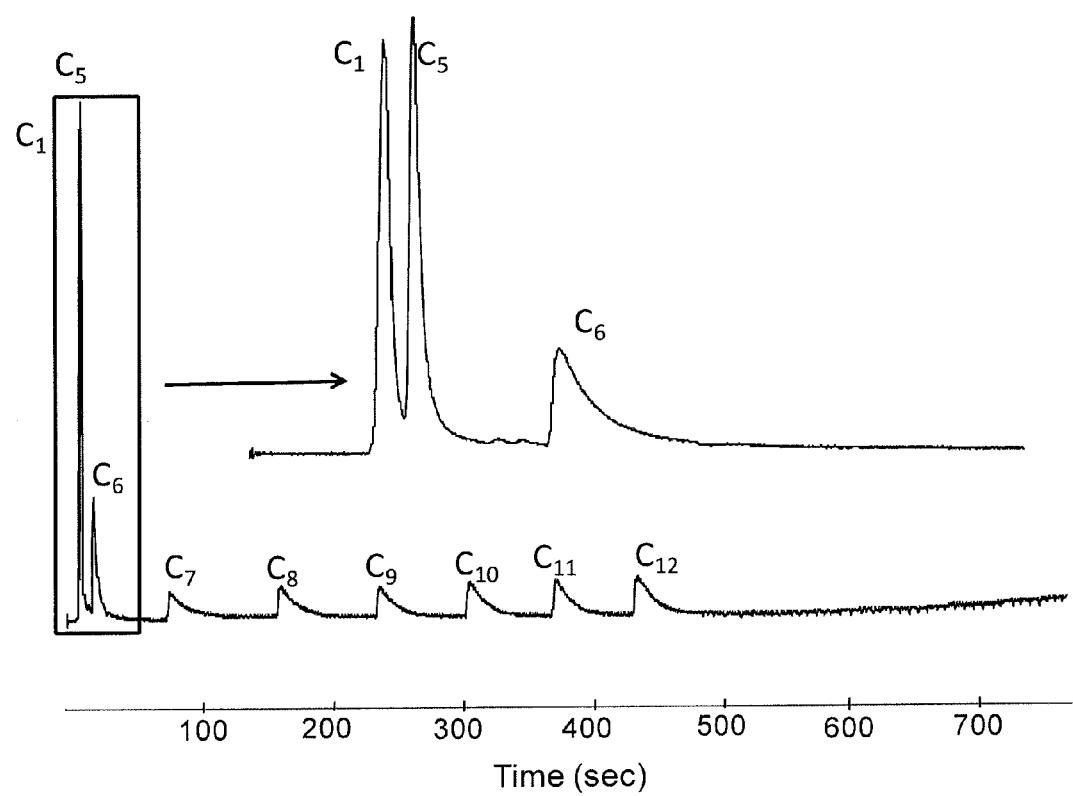
FIG. 12 is a gas chromatogram resulting from a VGC prepared by the electrochemical method disclosed herein.

An example chromatogram demonstrating a successful stationary phase coating using apparatus 100' of FIG. 6 is shown in FIG. 12. A 2-meter length of 304 stainless steel tubing with a 0.010" inner diameter (1/16" outer diameter) was coated with polyphenol stationary phase using apparatus 100' with a coating solution consisting of deionized water with a saturated concentration of NaOH (~25-28 mol/L) and 0.0050 mol/L phenol. Reference numbers below are referring to FIG. 6. A large area gold electrode severed as a counter electrode 142 and was immersed in a 1 mol/L solution of NaCl in the reservoir 116. A standard Ag/AgCl reference electrode 144 was also immersed in the reservoir 116. The potential of the tube 112 was linearly cycled with time (i.e. cyclic voltammetry) from 250 mV to 750 mV and back to 250 mV 630 times at a scan rate of 1 mV/sec. Because of the large "iR" drop in the tube, the conventional cyclic voltammogram was not observed (e.g. no oxidation peak was visible); however, larger anodic currents developed with time, consistent with the sequential growth of polyphenol layers. The column was washed with copious deionized water to remove residual ions and molecules, and then dried under nitrogen gas flow at room temperature for 72 hours. The column was then installed in a laboratory GC (thick end at inlet) and a series of chromatographic separations were performed to evaluate the column. The text mixture was a gaseous injection of methane, n-pentane, n-hexane, n-heptane, n-octane, n-nonane, n-decane, n-undecane, and n-dodecane. Because the column most likely has a thick stationary phase coating, a temperature program was employed to reduce analysis times to a more convenient length: the oven was held at 30° C. for 45 seconds, then ramped at 20° C./min until reaching 350° C. where it was held for the remainder of the experiment. The hydrogen carrier gas pressure was 2 psi. The injection pulse was proven to be small relative to the on-column band broadening by the procedure given above.

The example chromatogram in FIG. 12 shows the fully separated alkane peaks with insets to the left and right to more clearly show the early and late portions of the chromatogram with better graphical resolution. Upon repeated chromatographic analyses, it was found that the retention times for the alkanes in this separation were highly stable, indicating the polyphenol film is stable upon repeated temperature cycles up to 350° C.

The embodiments of this invention shown in the drawing and described above are exemplary of numerous embodiments that may be made within the scope of the appended claims. It is contemplated that numerous other configurations of the devices and methods may be created taking advantage of the disclosed approach. In short, it is the applicant's intention that the scope of the patent issuing herefrom will be limited only by the scope of the appended claims.

What is claimed is:

1. A method for depositing a stationary phase in a tube for chromatography, the method comprising:
    providing a tube having a first end and a second end, the tube containing a fluid composition comprising a stationary phase precursor and a solvent;
    connecting the first end of the tube to a flow device;
    removing the solvent from a meniscus of the fluid composition, the solvent exiting the tube at the second end; and
    operating the flow device while removing the solvent such that the amount of the stationary phase precursor deposited within the tube changes as the meniscus retreats within the tube to deposit a stationary phase having a thickness gradient along the length of the interior of the tube.

2. The method of claim 1 wherein the tube has a generally uniform cross-sectional area along its length, and the stationary phase has a generally reducing thickness from the first end to the second end of the tube.

3. The method of claim 1 wherein the tube has a generally enlarging cross-sectional area along its length; wherein the loading step includes introducing a decreasing concentration of the stationary phase precursor from one end of the tube to the other end thereof; wherein the stationary phase is deposited in the tube as a layer of generally uniform thickness.

4. The method of claim 1 wherein the tube has a generally non-uniform cross-sectional area along its length; wherein the loading step includes introducing a decreasing concentration of the stationary phase precursor; wherein the stationary phase is deposited in the tube as a layer of generally non-uniform thickness.

5. The method of claim 1 wherein the tube includes a narrower cross-sectional area at the first end relative to the cross-sectional area at the second end, and wherein the stationary phase has a generally reducing thickness from the first end to the second end.

6. The method of claim 1 wherein the removing step includes evaporating the solvent.

7. The method of claim 1 wherein the removing step includes controlling the temperature of the tube.

8. The method of claim 1 wherein the flow device includes a syringe pump, a high pressure liquid chromatography pump, a peristaltic pump, a gravity feed device, and combinations thereof.

9. The method of claim 1 wherein the tube includes a surface area-increasing member within the tube; wherein the stationary phase precursor is deposited on the surface area-increasing member.

10. The method of claim 1 wherein the stationary phase is thicker at the first end and is thinner at the second end of the tube.

11. The method of claim 10 wherein the stationary phase varies along the length of the tube as a linear or non-linear function from the first end to the second end.

12. The method of claim 1 wherein the flow device includes a syringe pump, a high pressure liquid chromatography pump, a peristaltic pump, a gravity feed device, or a combination thereof.

13. The method of claim 1 wherein the tube includes a surface area-increasing member within the tube; wherein the stationary phase precursor is deposited on the surface area-increasing member.

* * * * *